United States Patent
Rothberg et al.

(10) Patent No.: US 10,711,299 B2
(45) Date of Patent: Jul. 14, 2020

(54) PULSE CALLER AND BASE CALLER

(71) Applicant: Quantum-Si Incorporated, Guilford, CT (US)

(72) Inventors: Jonathan M. Rothberg, Guilford, CT (US); Craig Wenger, North Branford, CT (US); Mel Davey, Westbrook, CT (US); Keith G. Fife, Palo Alto, CA (US); Jimmy Jia, New York, NY (US); Brian Reed, Madison, CT (US); Brett J. Gyarfas, Guilford, CT (US)

(73) Assignee: Quantum-Si Incorporated, Guilford, CT (US)

( * ) Notice: Subject to any disclaimer, the term of this patent is extended or adjusted under 35 U.S.C. 154(b) by 0 days.

(21) Appl. No.: 15/611,573

(22) Filed: Jun. 1, 2017

(65) Prior Publication Data

US 2017/0349944 A1 Dec. 7, 2017

Related U.S. Application Data

(60) Provisional application No. 62/343,997, filed on Jun. 1, 2016.

(51) Int. Cl.
*C12Q 1/6869* (2018.01)
*G16B 30/00* (2019.01)
*G01N 21/64* (2006.01)

(52) U.S. Cl.
CPC ........ *C12Q 1/6869* (2013.01); *G01N 21/6428* (2013.01); *G16B 30/00* (2019.02); *G01N 2021/6439* (2013.01)

(58) Field of Classification Search
None
See application file for complete search history.

(56) References Cited

U.S. PATENT DOCUMENTS

| | | |
|---|---|---|
| 9,759,658 B2 | 9/2017 | Rothberg et al. |
| 9,885,657 B2 | 2/2018 | Rothberg et al. |
| 10,048,208 B2 | 8/2018 | Rothberg et al. |
| 10,068,053 B2 | 9/2018 | Kermani et al. |
| 10,108,778 B2 | 10/2018 | Colwell et al. |
| 10,185,803 B2 | 1/2019 | Frey et al. |
| 10,216,895 B2 | 2/2019 | Liu |
| 10,217,048 B2 | 2/2019 | Glode et al. |
| 2009/0024331 A1 | 1/2009 | Tomaney et al. |
| 2016/0041095 A1 | 2/2016 | Rothberg et al. |
| 2016/0084761 A1 | 3/2016 | Rothberg et al. |
| 2016/0133668 A1 | 5/2016 | Rothberg et al. |

FOREIGN PATENT DOCUMENTS

| | | |
|---|---|---|
| WO | WO 00/09753 A1 | 2/2000 |

OTHER PUBLICATIONS

International Preliminary Report on Patentability for International Application No. PCT/US2017/035420 dated Dec. 13, 2018.
Killick et al., Optimal Detection of Changepoints With a Linear Computational Cost. Journal of the American Statistical Association. 2012;107(500):1590-8.
Cao et al., A Simple Statistical Algorithm for Biological Sequence Compression in Data Compression Conference. 2007 (IEEE, Utah), pp. 43-52.
International Search Report and Written Opinion for International Application No. PCT/US2019/015098 dated Apr. 30, 2019.
Albrecht et al., Deep learning for single-molecule science. Nanotechnology. 2017;28(42):423001.
Baylor et al., TFX: A TensorFlow-Based Production-Scale Machine Learning Platform. Knowledge Discovery and Data Mining. ACM. 2017;1387-95.
Sutskever et al., Sequence to Sequence Learning with Neural Networks. arXiv. 2014;1-9.
Teng et al., Chiron: Translating nanopore raw signal directly into nucleotide sequence using deep learning. BioRxiv. 2017.
U.S. Appl. No. 16/258,299, filed Jan. 25, 2019, Rothberg et al.

*Primary Examiner* — Joseph Woitach
(74) *Attorney, Agent, or Firm* — Wolf, Greenfield & Sacks, P.C.

(57) ABSTRACT

System and methods for identifying nucleotides based on data acquired from a sensor during sequencing of nucleic acids. The method may include obtaining characteristics of light detected from luminescent labels associated with the nucleotides during nucleotide incorporation events. The characteristics may include, for each nucleotide incorporation event, a temporal characteristic the light and an intensity characteristic of the light. The temporal characteristic representing a speed of decay of a probability of photon emission by a luminescent label after excitation. The method may further include grouping points representing the characteristics of the nucleotide incorporation events into groups of points. The individual points may represent at least the temporal characteristic and the intensity characteristic for a corresponding nucleotide incorporation event. The method may further include assigning the groups of points to individual nucleotides.

14 Claims, 12 Drawing Sheets

PULSE CALLER AND BASE CALLER

RELATED APPLICATIONS

This application claims priority to U.S. Provisional Patent Application 62/343,997, titled "PULSE CALLER AND BASE CALLER," filed Jun. 1, 2016, which is hereby incorporated by reference in its entirety.

BACKGROUND

Sequencing of nucleic acids (e.g., deoxyribonucleic acid (DNA), ribonucleic acid (RNA)) includes identifying individual of nucleotides in a target nucleic acid. Some nucleic acid sequencing methods include identifying individual nucleotides as they are incorporated into nucleic acid strand complementary to the target nucleic acid. The series of nucleotides for the complementary strand identified during the sequencing process may then allow for identification of the nucleotide sequence for the target nucleic acid strand.

SUMMARY

Some embodiments relate to a method that includes receiving first time-bin information regarding the times at which a first luminescent label emits light in response to excitations of the first luminescent label, calculating first light intensity information based on the first time-bin information, receiving second time-bin information regarding the times at which a second luminescent label emits light in response to excitations of the second luminescent label, calculating second light intensity information based on the second time-bin information, and calculating times at which nucleotide incorporation events occur using the first and second light intensity information.

The calculating of the times at which the nucleotide incorporation events occur may be performed using a pulse identification algorithm. The pulse identification algorithm may include a changepoint algorithm, a running mean/median and variance algorithm or a state machine algorithm. Calculating the first light intensity information may include summing the first time-bin information, and calculating the second light intensity information may include summing the second time-bin information.

Some embodiments relate to a method that includes receiving first time-bin information regarding times at which a first luminescent label emits first light in response to excitations of the first luminescent label and calculating a first temporal characteristic of the first light based on the first time-bin information. The temporal characteristic may represent a speed of decay of a probability of photon emission by the first luminescent label after excitation. The method may further include receiving second time-bin information regarding times at which a second luminescent label emits second light in response to excitations of the second luminescent label and calculating a second temporal characteristic of the second light based on the second time-bin information. The second temporal characteristic may represent a speed of decay of a probability of photon emission by the second luminescent label after excitation. The method may further include calculating times at which nucleotide incorporation events occur using the first and second temporal characteristics.

The calculating of the times at which the nucleotide incorporation events occur may be performed using a pulse identification algorithm. The pulse identification algorithm may include a changepoint algorithm, a running mean/median and variance algorithm or a state machine algorithm.

Some embodiments relate to a method that includes determining one or more temporal characteristics representing a speed of decay of a probability of photon emission by one or more luminescent labels after excitation and calculating times at which nucleotide incorporation events occur using the at least one temporal characteristic.

The calculating of the times at which nucleotide incorporation events occur may be also performed using an intensity of light emitted by the one or more luminescent labels.

Some embodiments relate to a method that includes receiving time-bin information regarding times at which a luminescent label emits light in response to excitations of the luminescent label, calculating light intensity information based on the time-bin information, and calculating a time at which at least one nucleotide incorporation event occurs using the light intensity information.

The time at which at least one nucleotide incorporation event occurs may be also performed using a temporal characteristic of the light.

Some embodiments relate to a method of identifying nucleotides that includes obtaining characteristics of light detected from luminescent labels associated with the nucleotides during nucleotide incorporation events. The characteristics may include, for each nucleotide incorporation event: i) a temporal characteristic the light, the temporal characteristic representing a speed of decay of a probability of photon emission by a luminescent label after excitation; and ii) an intensity characteristic of the light. The method may further include grouping points representing the characteristics of the nucleotide incorporation events into groups of points, individual points representing at least the temporal characteristic and the intensity characteristic for a corresponding nucleotide incorporation event, and assigning the groups of points to individual nucleotides.

The temporal characteristic may include a luminance lifetime or a ratio of photons detected in different time bins. The grouping of the points may be performed by a clustering algorithm. The clustering algorithm may perform k-means clustering in which k is greater than or equal to four. The individual groups of points may be assigned to individual nucleotides based on predetermined light-emitting characteristics of the luminescent labels.

Some embodiments relate to a method of calibrating a sequencing instrument, the method includes obtaining characteristics of light detected from luminescent labels associated with the nucleotides during nucleotide incorporation events. The characteristics may include, for each nucleotide incorporation event: i) a temporal characteristic the light, the temporal characteristic representing a speed of decay of a probability of photon emission by a luminescent label after excitation; and ii) an intensity characteristic of the light. The method may further include grouping points representing the characteristics of the nucleotide incorporation events into groups of points, individual points representing at least the temporal characteristic and the intensity characteristic for a corresponding nucleotide incorporation event, assigning individual groups of points individual nucleotides, determining one or more criteria distinguishing the groups of points, and storing the one or more criteria.

The one or more criteria may include one or more boundaries between the groups of points. The one or more criteria may include centroids of the groups of points. The one or more criteria may be stored in non-volatile memory. Grouping the points may include running a clustering algorithm on the points.

Some embodiments relate to a method of identifying nucleotides, the method includes obtaining characteristics of light detected from luminescent labels associated with the nucleotides during nucleotide incorporation events. The characteristics may include, for each nucleotide incorporation event: i) a temporal characteristic of the light, the temporal characteristic representing a speed of decay of a probability of photon emission by a luminescent label after excitation; and ii) an intensity characteristic of the light. The method may further include assigning the nucleotide incorporation events to nucleotides by evaluating the temporal characteristic and the intensity characteristic in view of stored criteria for a sequencing instrument distinguishing between the characteristics of the light for the luminescent labels.

The stored criteria may include one or more boundaries between characteristics of the luminescent labels for different nucleotides. The assigning of the nucleotide incorporation events may include comparing a point representing the temporal characteristic and the intensity characteristic with the one or more boundaries. The one or more stored criteria may include centroids of groups of points, each group corresponding to a respective nucleotide. The assigning of the nucleotide incorporation events may include determining distances between a point representing the temporal characteristic and the intensity characteristic for an incorporation event to the centroids and assigning the nucleotide incorporation event to a nucleotide with a centroid closest to the point. The stored criteria may be calibration criteria stored in non-volatile memory.

Some embodiments relate to a method of identifying nucleotides, including obtaining characteristics of light detected from luminescent labels associated with the nucleotides during nucleotide incorporation events. The characteristics may include, for each nucleotide incorporation event: i) a temporal characteristic the light, the temporal characteristic representing a speed of decay of a probability of photon emission by a luminescent label after excitation; and ii) a second characteristic of the light. The method may further include grouping points representing the characteristics of the nucleotide incorporation events into groups of points, individual points representing at least the temporal characteristic and the intensity characteristic for a corresponding nucleotide incorporation event, and assigning the groups of points to individual nucleotides.

Some embodiments relate to a method of calibrating a sequencing instrument, including obtaining characteristics of light detected from luminescent labels associated with the nucleotides during nucleotide incorporation events. The characteristics may include, for each nucleotide incorporation event: i) a temporal characteristic the light, the temporal characteristic representing a speed of decay of a probability of photon emission by a luminescent label after excitation; and ii) a second characteristic of the light. The method may further include grouping points representing the characteristics of the nucleotide incorporation events into groups of points, individual points representing at least the temporal characteristic and the intensity characteristic for a corresponding nucleotide incorporation event, assigning individual groups of points individual nucleotides, determining one or more criteria distinguishing the groups of points, and storing the one or more criteria.

Some embodiments relate to a method of identifying nucleotides, including obtaining characteristics of light detected from luminescent labels associated with the nucleotides during nucleotide incorporation events. The characteristics may include, for each nucleotide incorporation event: i) a temporal characteristic the light, the temporal characteristic representing a speed of decay of a probability of photon emission by a luminescent label after excitation; and ii) an intensity characteristic of the light. The method may further include assigning the nucleotide incorporation events to nucleotides by evaluating the temporal characteristic and the second characteristic in view of stored criteria for a sequencing instrument distinguishing between the characteristics of the light for the luminescent labels.

Some embodiments relate to a method including obtaining characteristics of light detected from luminescent labels associated with the nucleotides during nucleotide incorporation events. The characteristics may include, for each nucleotide incorporation event: i) a temporal characteristic the light, the temporal characteristic representing a speed of decay of a probability of photon emission by a luminescent label after excitation; and ii) an intensity characteristic of the light. The method may further include determining one or more criteria distinguishing groups of points representing the characteristics of the nucleotide incorporation events, individual points representing the temporal characteristic and the intensity characteristic for a corresponding nucleotide incorporation event.

The method may further include assigning the groups to respective nucleotides to produce nucleotide assignments for the groups. The method may further include assigning the points to nucleotides based on the one or more criteria and the nucleotide assignments for the groups.

Some embodiments relate to a method including obtaining characteristics of light detected from luminescent labels associated with the nucleotides during nucleotide incorporation events. The characteristics may include, for each nucleotide incorporation event: i) a temporal characteristic the light, the temporal characteristic representing a speed of decay of a probability of photon emission by a luminescent label after excitation; and ii) a second characteristic of the light. The method may further include determining one or more criteria distinguishing groups of points representing the characteristics of the nucleotide incorporation events, individual points representing the temporal characteristic and the second characteristic for a corresponding nucleotide incorporation event.

Some embodiments relate to a non-transitory computer readable storage medium having stored thereon instructions, which, when executed by a processor, performs any of the methods described herein.

Some embodiments relate to an apparatus including a processor configured to perform any of the methods described herein.

Some embodiments relate to a sequencing instrument, including a photodetector configured to receive light from luminescent labels during a sequencing reaction and a processor configured to perform any of the methods described herein.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIG. 2-1A is a block diagram representation of an apparatus that may be used for rapid, mobile analysis of biological and chemical specimens, in accordance with some embodiments.

FIG. 2-1B is a block diagram of an integrated device and an instrument, in accordance with some embodiments.

FIG. 3-1A is a schematic of an integrated device, in accordance with some embodiments.

FIG. 3-1B is a schematic of excitation energy coupling to sample wells in a row of pixels and emission energy from each sample well directed towards sensors, in accordance with some embodiments.

DETAILED DESCRIPTION

Figure 1A:
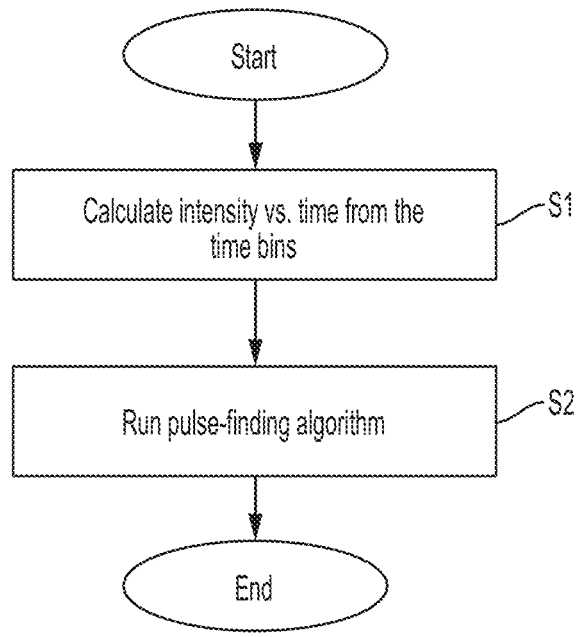
FIG. 1A is a flowchart of an algorithm implemented by a pulse caller, in accordance with some embodiments.

The techniques described herein relate to sequencing of nucleic acids, such as DNA and RNA, and in particular to techniques for identifying nucleotides based upon data acquired from a sensor. Nucleic acid sequencing allows for the determination of the order and position of nucleotides in a target nucleic acid. Some nucleic acid sequencing methods are based on sequencing by synthesis, in which the identity of a nucleotide is determined as the nucleotide is incorporated into a newly synthesized strand of nucleic acid that is complementary to the target nucleic acid. During sequencing, a polymerizing enzyme (e.g., DNA polymerase) may couple (e.g., attach) to a priming location of a target nucleic acid molecule and add or incorporate nucleotides to the primer via the action of the polymerizing enzyme, which can be generally referred to as a primer extension reaction.

Each nucleotide may be associated with a luminescent molecule (e.g., fluorophore) that emits light in response to excitation, and which is used to label each type of nucleotide to discriminate among the different types of nucleotides. For example, a set of four labels may be used to label the nucleobases present in DNA such that each marker of the set is associated with a different nucleobase, e.g., a first label being associated with adenine (A), a second label being associated with cytosine (C), a third label being associated with guanine (G), and a fourth label being associated with thymine (T). A label may be coupled to a nucleotide through bonding of the label to the nucleotide either directly or indirectly via a linker molecule.

As the primer extension reaction occurs, a nucleotide and its respective luminescent labels are retained by the polymerizing enzyme during incorporation of the nucleotide into the synthesized complementary nucleic acid. The luminescent label can be excited by pulses of light during the period in which the nucleotide is incorporated into the synthesized nucleic acid and emits light characteristic of the label. In some embodiments, the label is attached, either directly or indirectly through a linker molecule, to a terminal phosphate of a nucleotide such that the label is detached or released from the nucleotide via the action of the polymerizing enzyme during incorporation of the nucleotide (e.g., cleavage of a phosphate bond). Sensing and analyzing the light emitted by the luminescent label in response to the excitation can allow identifying the nucleotide that was incorporated. As the primer extension reaction occurs, excitation, sensing and analysis is performed for each subsequent nucleotide added to the synthesized nucleic acid. The sequence of the target nucleic acid can be determined from the complementary sequence of the synthesized nucleic acid.

The light emitted by the luminescent label may have a number of characteristics that can be used to distinguish the label from other labels, and thus identify a nucleotide. These characteristics include intensity (e.g., probability of emitting light), a temporal characteristic (e.g., rate of decay of the probability of photon emission after excitation, pulse duration for incorporation and/or interpulse duration before and/or after incorporation), a spectral characteristic (e.g., wavelength(s) of light emitted), or any combination thereof. The light emitted by the luminescent label may be detected by a photodetector that can detect one or more of these characteristics. An example of a suitable photodetector is described in U.S. patent application Ser. No. 14/821,656 entitled "INTEGRATED DEVICE FOR TEMPORAL BINNING OF RECEIVED PHOTONS," which is hereby incorporated by reference in its entirety. As described therein, the photodetector may have the capability of detecting the arrival times of photons, which can allow determining temporal characteristics of the light emitted by the labels. Detecting temporal characteristics of the emitted light can allow for discriminating between labels that emit light with different temporal characteristics. One example of a temporal characteristic is luminance lifetime. A luminescent molecule, such as a fluorophore, may emit photons in response to excitation. The probability of the luminescent molecule emitting a photon decreases with time after the excitation occurs. The rate of decay in the probability may be exponential. The "lifetime" is characteristic of how fast the probability decays over time. A fast decay is said to have a short lifetime, while a slow decay is said to have a long lifetime. Detecting temporal characteristics of the light emitted by luminescent molecules can allow distinguishing luminescent molecules that have different lifetimes. Labeling different nucleotides with luminescent molecules having different lifetimes can allow distinguishing between the nucleotides based upon a temporal characteristic of the light detected.

The photodetector described in U.S. patent application Ser. No. 14/821,656 can detect the time of arrival of photons with nanosecond or picosecond resolution, and can time-bin the arrival of incident photons. Since the emission of photons is probabilistic, the label may be excited a plurality of times and any resulting photon emissions may be time-binned. Performing such a measurement a plurality of times allows populating a histogram of times at which photons arrived after an excitation event. This information can be analyzed to calculate a temporal characteristic of the emitted light, which can allow distinguishing the label from another label based on the temporal characteristic.

The techniques described herein can analyze a stream of data from a photodetector to sequence the nucleic acid based on the characteristics of the detected light. These techniques may be implemented by a "pulse caller" and a "base caller," which may be software and/or hardware modules of a sequencing instrument or another device. Generally, a pulse caller analyzes the stream of data to identify time periods when pulses of luminescence from the label occur, signifying a dye-conjugated nucleotide being incorporated into the oligonucleotide strand by the polymerase. A "base caller" analyzes characteristics of the light detected during the time periods identified by the pulse caller to determine, or "call" the identity of the nucleotides.

FIG. 1A shows a flowchart of an algorithm that may be implemented by the pulse caller. In step S1, the intensity of the received light vs. time is calculated. As discussed above, the photodetector may time bin the arrival of incident photons from a label in response to exposing the label to an excitation source (e.g., by a laser pulse). A label may be repeatedly excited, and the arrival of incident photons from the label may be time binned. As an example, during a 10 ms measurement period, laser excitation pulses may be emitted at a frequency of 100 MHz to excite the label. The label may emit a photon with a low probability (e.g., 1 photon emission in 10,000 excitations). If the label is excited a number of times (e.g., 1 million times) within a 10 ms period, approximately 100 photons may be received. In some instances, a label may not become excited after exposure to an excitation source and not emit a photon after an excitation event, which may contribute to the low probability of emission. As discussed above, the arrival times of the incident photons with respect to the excitation may be time-binned. The photodetector may provide signals representing the number of photons in each time bin.

Figure 1B:
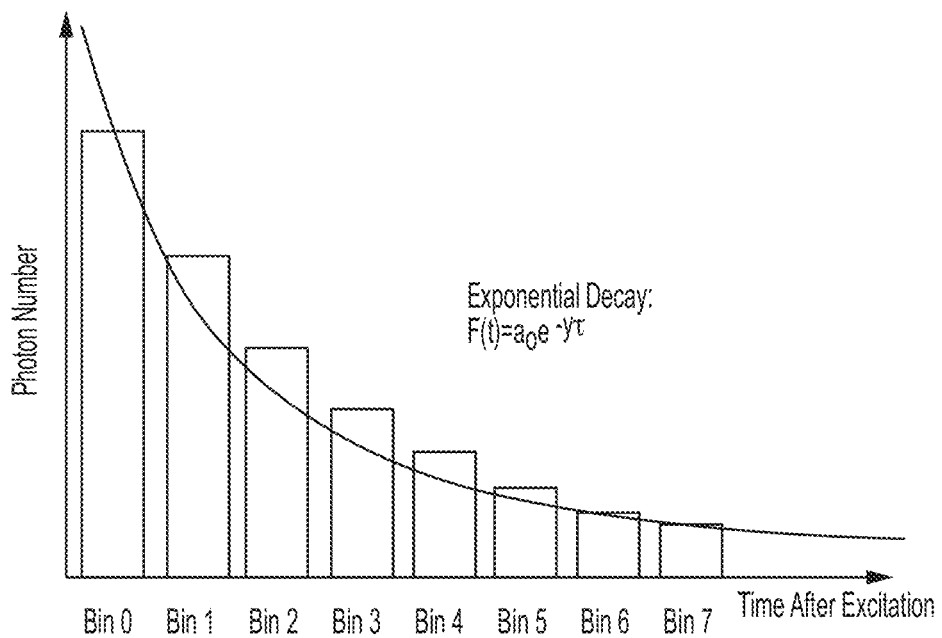
FIG. 1B is a plot of probability of photon emission over time after excitation and the distribution of the number of photons in time bins detected by a photodetector, in accordance with some embodiments.

FIG. 1B shows an example in which a photodetector time-bins the arrival of incident photons into eight time bins. Since, as discussed above, the probability of photon emission decays over time, earlier time bins have more photons than the later time bins. By repeatedly exciting the label and detecting the timing of photons emitted, a histogram can be populated that approximates the decay in the probability of photon emission over time, as shown in FIG. 1B.

The intensity of the light received over the measurement period (e.g., 10 ms) may be calculated by the pulse caller by summing the values representing the number of photons received in each time bin. For example, if the photodetector bins the arrival of incident photons into eight time bins, as shown in FIG. 1B, the number of photons received in the eight time bins are summed to determine the intensity. However, any number of time bins may be used. If the photodetector has two time bins, the values representing the number of photons received in both time bins are summed to determine the intensity. For example, if the first time bin has 100 photons and second time bin has 50 photons, these values may be summed to determine an intensity of 150 photons. Alternatively, a separate time bin may exist for the purpose of measuring the total photon intensity.

The determination of the intensity of the light received may be performed for subsequent measurement periods in the data stream from the photodetector. For example, if the photodetector performs measurements in 10 ms periods, the intensity may be determined for each measurement period by summing the time bins in each 10 ms period. As a result, data representing the intensity of the light received over time can be determined.

Figure 2:
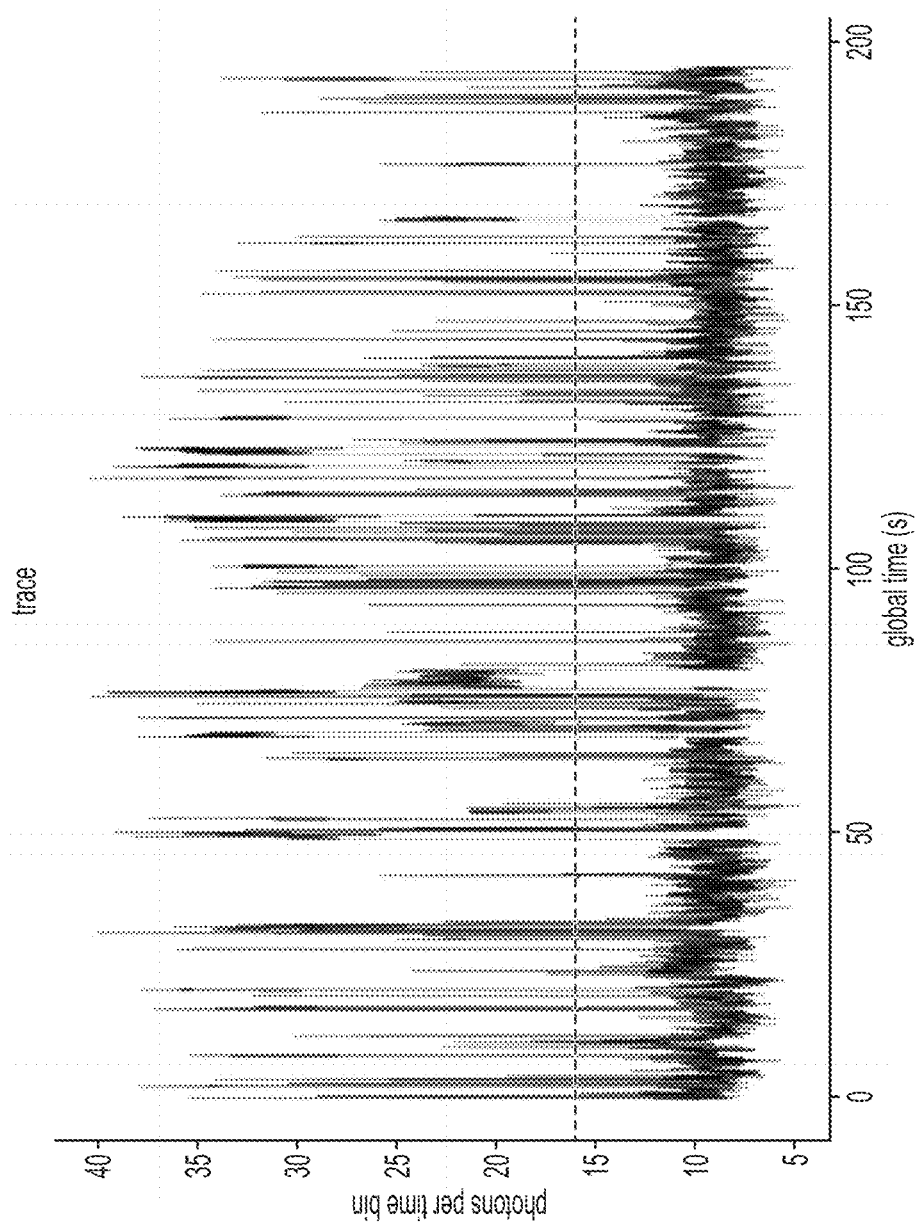
FIG. 2 is a plot of intensity of light detected by a photodetector over time during sequencing of a nucleic acid, in accordance with some embodiments.
Figures 1A, 2:
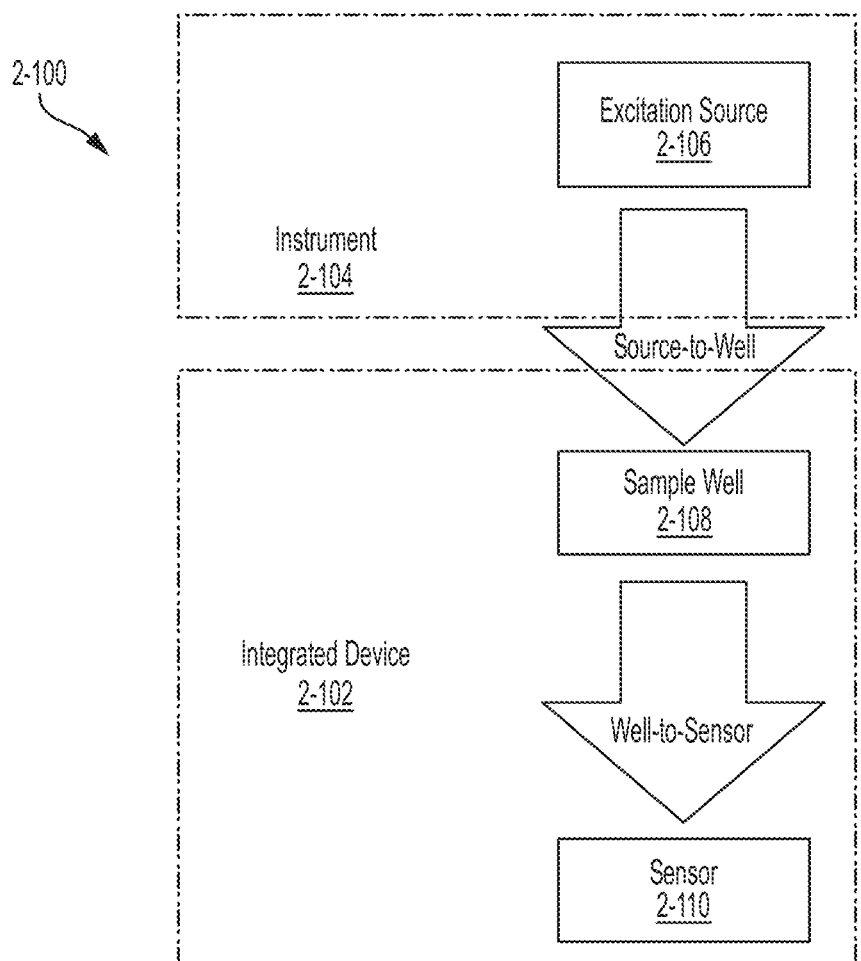
Figures 1B, 2:
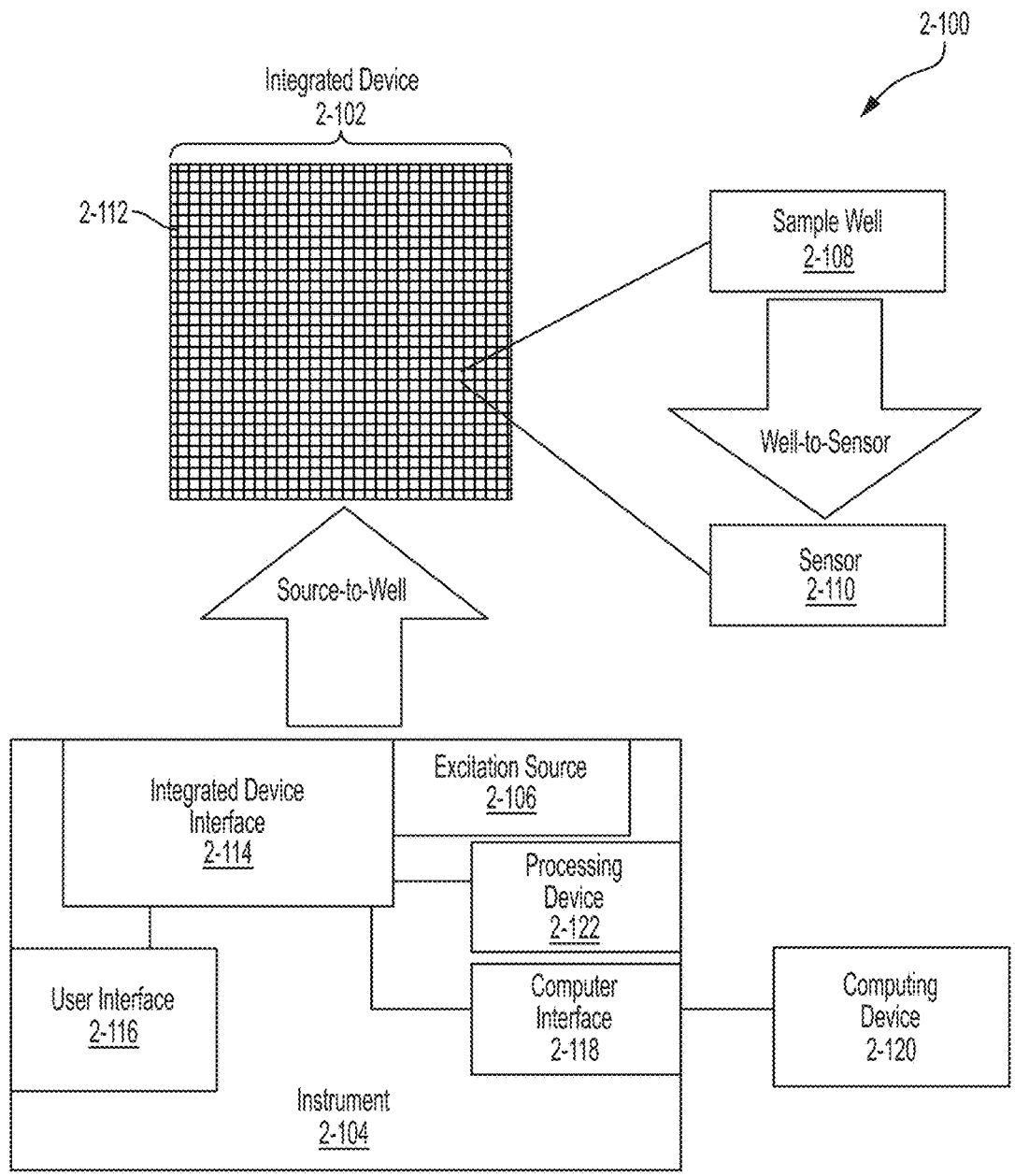

FIG. 2 shows several minutes of an example trace representing the intensity of the light received vs. time. Because there is significant baseline and variance in the trace and true pulses often have a low signal-to-noise ratio, identifying pulses corresponding to incorporation events can be challenging. In step S2, a pulse-finding algorithm is run on the intensity vs. time data to identify times when bursts of light are emitted corresponding to incorporation events.

For the pulse-finding algorithm, one suitable approach is to run a changepoint algorithm on the trace data that determines when shifts in the mean and variance of the signal occur, e.g., when changing from background (i.e., interpulse) to signal (i.e. pulse) and vice versa. After each changepoint is identified, a threshold separates interpulse regions (regions between pulses) from pulse regions on the basis of changepoint level (e.g., intensity). This threshold can be determined manually, with histogramming, kernel density estimation, or k-means clustering.

Another suitable approach is to analyze the mean/median and variance of the trace, and then define pulses as increases of a certain number of standard deviations or more above the mean/median.

Yet another suitable approach is to use a state machine, which is either in a pulse or interpulse state, and is judged to alternate between the two. Thresholds define transitions between the two states.

In some embodiments, additional filtering of called pulses may occur, such as removing pulses that do not meet a minimum or maximum duration thresholds (as very short pulses and very long pulses are often false positives).

The latter two approaches have an additional benefit in that they can be operated on the data as it is being acquired, whereas the changepoint algorithm may need all of the data in order to operate.

Above is described techniques for identifying pulses corresponding to nucleotide incorporation events based on the intensity of the light emitted. However, other characteristics of the light emitted may be used to identify pulses in addition to, or as alternative to intensity. In some embodiments pulses may be identified based on temporal characteristic(s) of the emitted light as an alternative to or in addition to using intensity. Different nucleotides may be labeled with molecules that emit light with different temporal characteristics, and the temporal characteristics may be analyzed to determine when incorporation events begin and end. As an example, different luminescent labels may have different "lifetimes" or rates at which the probability of photon emission in response to excitation decays over time. A change in the measured lifetime may indicate the start or end of an incorporation event.

Figure 1C:
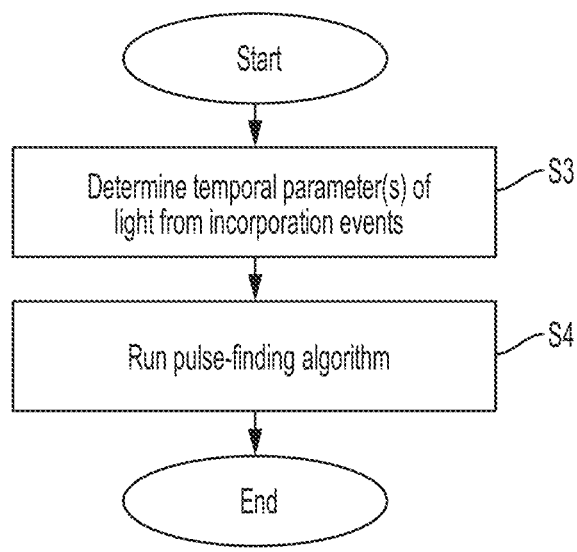
FIG. 1C is a flowchart of a method for determining nucleotide incorporation events using temporal parameter(s) of emitted light, in accordance with some embodiments.

FIG. 1C shows a flowchart of a method that uses temporal parameter(s) to determine when pulses corresponding to incorporation events occur. In step S3, temporal parameter(s) for the light emitted during incorporation events is/are determined. For example, as discussed below, temporal characteristics may be determined based upon time bin information (i.e., information from or based on or more time bins). In some embodiments, temporal characteristic(s) may be determined by the base caller and provided to the pulse caller. In step S4, a pulse-finding algorithm may be run on data representing the temporal parameter over time. The pulse-finding algorithm may operate similarly as discussed above with respect to intensity.

Figure 1D:
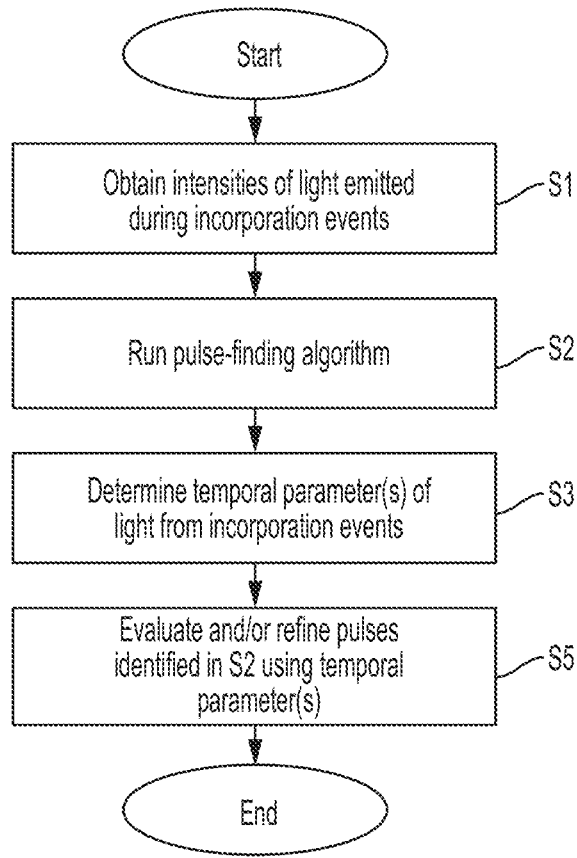
FIG. 1D is a flowchart of a method for determining nucleotide incorporation events using intensity and temporal characteristic(s) of emitted light, in accordance with some embodiments

In some embodiments, both intensity and temporal characteristic(s) may be used to identify the times at which incorporation events occur. As an example, changes in a temporal characteristic may be used to refine the identification of pulses based on intensity. FIG. 1D shows a flowchart of such a method. In step S1, intensities of light may be obtained for each incorporation event. The intensities may be calculated by summing the time bins in each set of time bins, as discussed above. However, the intensities need not be obtained by summing the time bins, and may be measured and/or determined in a different way. In step S2, a pulse-finding algorithm is run on the intensity vs. time data to identify times when bursts of light are emitted corresponding to incorporation events. In step S3, temporal parameter(s) for the light emitted during incorporation events is/are determined. In step S5, the pulses identified in step S2 may be evaluated and possibly refined based on the temporal parameter(s). For example, if a long pulse is identified (e.g., having a length greater than a threshold amount), the temporal parameter(s) of the light emitted during the pulse may be evaluated. If the temporal parameter shifts significantly during the pulse (e.g., changes by more than a threshold amount, or an amount that may indicate a different nucleotide), the initial pulse-call may be revised to identify two separate pulses instead of one long pulse. The time at which the shift in temporal parameter occurs may correspond to a temporal boundary between the two pulses. If the temporal parameter does not shift significantly during the pulse (e.g., does not change or changes by a relatively small amount), the initial pulse-call may be left unchanged. Accordingly, the results of initial pulse-calling based upon intensity can be evaluated and/or refined using temporal parameter(s).

In some embodiments, initial pulse-calling may be performed using temporal parameter(s), and pulses may be refined using intensity information.

As a result of running the pulse-finding algorithm, the pulse caller identifies the times at which pulses corresponding to incorporation events occur. For each pulse, the pulse-caller may identify the start-time and the stop-time, the start-time and the duration, or the stop-time and the duration. The times at which such pulses occur may be analyzed to identify the luminescent label, and thus its associated nucleotide.

After calling the pulse caller on a stream of data from the photodetector, the base caller may be called to analyze one or more characteristics of the light for each incorporation event. The pulse caller may pass the times at which pulses occur to the base caller. Optionally the pulse caller may pass additional information to the base caller, such as the information regarding the number of photons received in each time bin, the calculated intensity for each measurement period, or any other suitable information.

Figure 3:
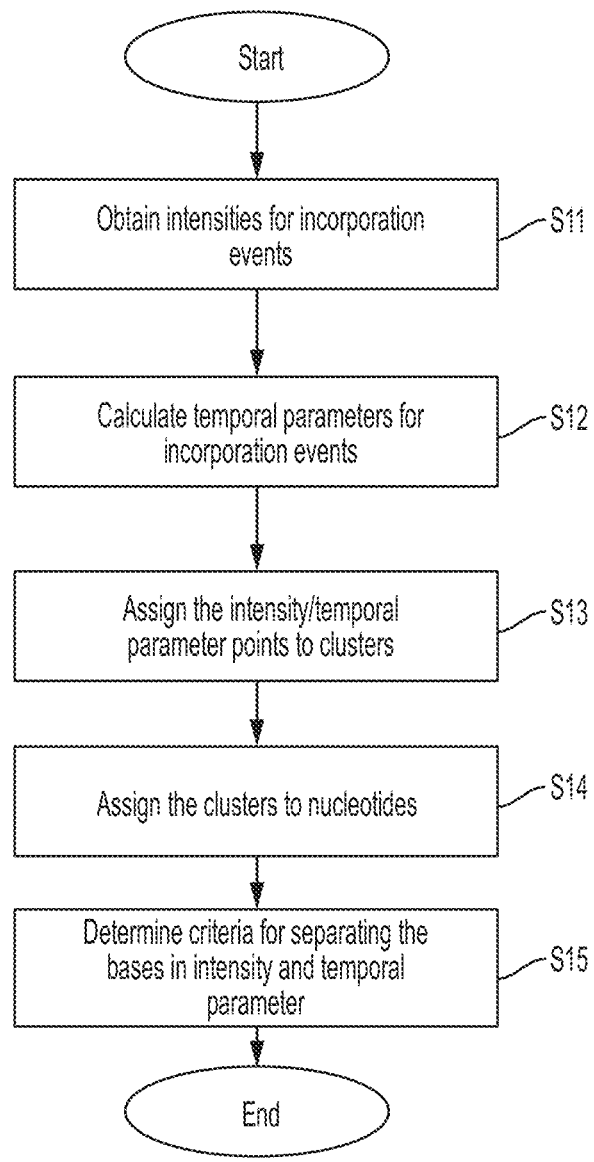
FIG. 3 is a flowchart of an algorithm implemented by a base caller, in accordance with some embodiments.
Figures 1A, 3:
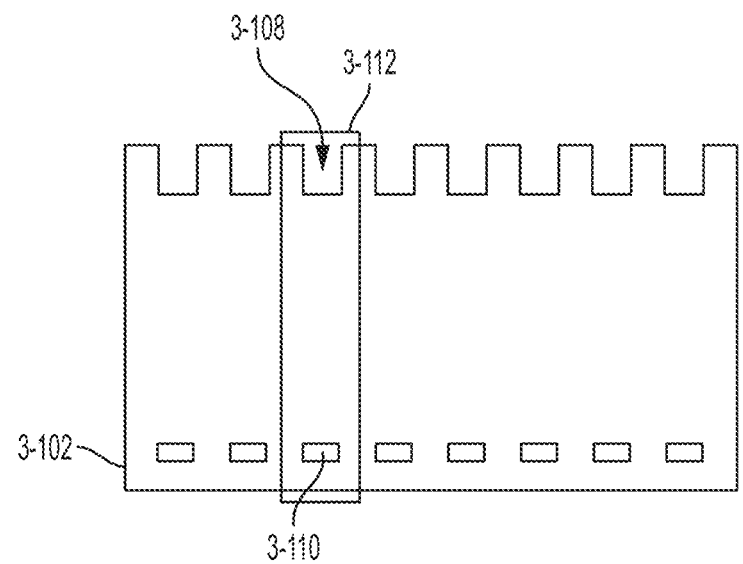
Figures 1B, 3:
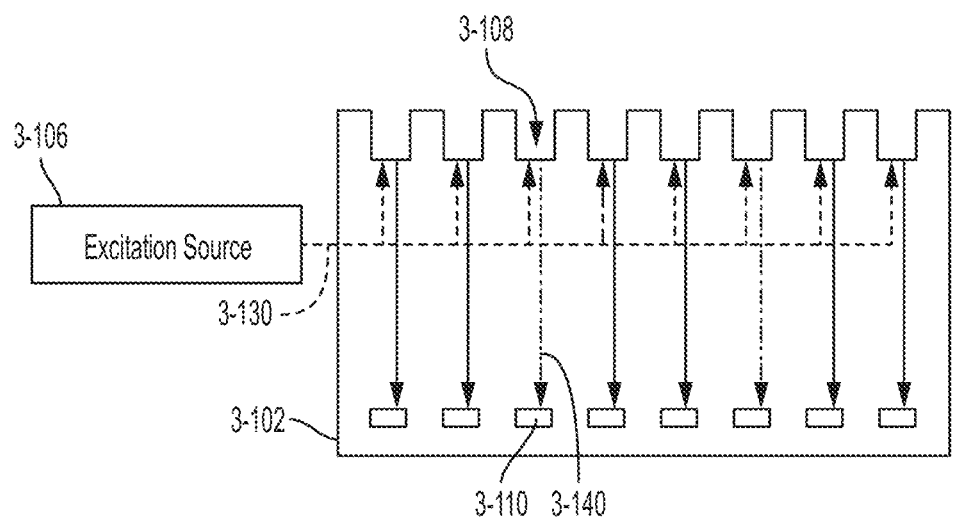

FIG. 3 shows a flowchart of an algorithm that may be implemented by the base caller to identify nucleotides, and/or may be used to calibrate the sequencing instrument.

In step S11, intensities may be obtained for each incorporation event. The intensities may be calculated by summing the time bins in each set of time bins, as discussed above. Alternatively, the base caller may receive the intensities from the pulse caller.

An intensity may be normalized for the duration of the incorporation event identified by the pulse caller. For example, if an incorporation event lasts for twice as long as a measurement interval, the intensity may be calculated by summing the time bins for the two measurement intervals and dividing by 2. For instance, if an incorporation event last 20 ms, the measurement period is 10 ms, and photons are grouped into two time bins, the intensity may be calculated by summing the photons collected in the two time bins of the first measurement as well as the photons collected in the two time bins of the second measurement, then dividing by two. Such a calculation may also be considered to be the calculation of an average intensity over the 20 ms incorporation event.

In step S12, a temporal parameter may be determined for each incorporation event. The temporal parameter may represent the decay in the probability of photon emission by a label over time following excitation. Any suitable temporal parameter may be used. In some embodiments the luminance lifetime may be calculated by fitting an exponential to the time bins (see e.g., FIG. 1B), and the luminance lifetime may be used as the temporal parameter. In some embodiments, the photon count for different time bins (or a value representative thereof) may be compared to determine a temporal parameter representing the decay in the probability of photon emission over time. For example, if the arrival of incident photons is binned into two time bins, the ratio of the photon count for the two bins may be calculated, and the ratio may be used as the temporal parameter. In some embodiments, the ratio of the bins may be a proxy for calculating a luminance lifetime. The ratio may be calculated in any suitable way. In some embodiments, if two time bins are used, the photon count for the time bin closest in time to the excitation event may be divided by the photon count for the second time bin to produce the ratio. In some embodiments, the photon count of the time bins or the value representative thereof may be normalized (e.g., by the summed intensity over a set of time bins), and the normalized values may be used to determine the temporal parameter. In some embodiments, the time bin with the maximum photon count may be used as the temporal parameter. To determine the time bin with the maximum photon count, the photon counts for the time bins may be compared with one another. As an example with two time bins, the photon count for a first time bin may be compared with the photon count for a second time bin. The bin with the higher photon count may be selected as a temporal parameter, and may be used for discriminating luminescent molecules. For example, one luminescent molecule may have a relatively short lifetime, which may result in the first time bin (closest in time to the excitation event) having the maximum photon count, and another luminescent molecule may have a relatively long lifetime, which may result in another time bin (farther in time from the excitation event) having the maximum photon count.

Although FIG. 3 shows step S11 as being performed prior to step S12, this is merely by way of illustration, as step S12 may be performed prior to step S11, or steps S11 and S12 may be performed concurrently.

Figure 4:
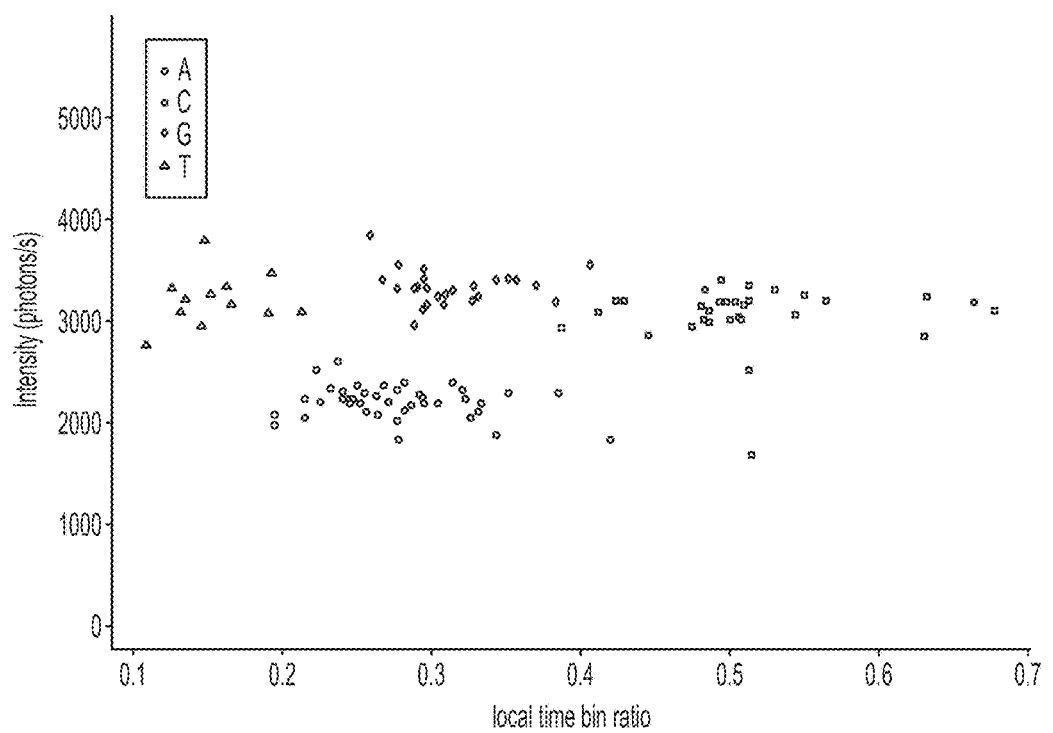
FIG. 4 is a plot of intensity versus time bin ratio as a temporal parameter for nucleotide incorporation events showing clusters of points for different nucleotides, in accordance with some embodiments.

FIG. 4 shows that the intensity and temporal parameter for each incorporation event may be plotted as a point in two-dimensional space, with intensity and temporal parameter being on respective axes. In this example, the temporal parameter is plotted on the horizontal (x) axis and intensity is plotted on the vertical (y) axis. Four different labels may be used for the nucleotides that can be distinguished from one another based upon the intensity, the temporal parameter, or both. As shown in FIG. 4, plotting the measured intensity and temporal parameter for each incorporation event results in four clusters of points corresponding to the four nucleotides A, C, G and T.

In step S13, the points may be assigned to groups (also referred to herein as "clusters"). In some embodiments, a clustering algorithm may be run on the points to assign the points for each incorporation event to one of four clusters. For example, the clustering algorithm may perform k-means clustering of the pulses in n-dimensional space, where k is 4 (A, C, G, T), and n is the number of metrics being used for base-calling. However, in some embodiments more than four clusters may be assigned. If more than four clusters are assigned, clustering may be performed in which k is greater than 4. The inventors have recognized and appreciated that in some cases the clusters may not be well-resolved, and it may be advantageous to group the points into more than four clusters. In such a case, more than one cluster may be assigned to the same nucleotide. In some embodiments, filtering may be performed to eliminate points that are outliers. For example, if a point has a temporal parameter and/or intensity that is outside of an expected range, it may be excluded from the clustering algorithm and/or may not be assigned to any nucleotide group.

Any suitable number of points may be provided to the clustering algorithm, such as greater than 50, greater than 100, greater than 500, etc. The result of the clustering algorithm is to group each point into one of the four (or more) clusters. In the example of FIG. 4, n=2 because two metrics, intensity and temporal parameter, are used. A two-dimensional example with intensity and time bin ratio as a temporal parameter is plotted in FIG. 4. However, other metrics may be used.

Another two-dimensional example involves obtaining both a temporal parameter and a spectral parameter, with the spectral parameter being on the vertical (y) axis of FIG. 4 rather than intensity. In this example, spectral information is obtained regarding the light emitted for each incorporation event, and used for distinguishing the nucleotides.

However, any number of metrics may be used, not limited to two. For example, in some embodiments spectral information for an incorporation event may be obtained in addition to intensity and a temporal parameter, which can be plotted as points in three-dimensional space, with intensity, temporal parameter, and spectral information being on respective axes.

After grouping the points, it may be beneficial to further refine the groups, potentially with more metrics than were used in the initial grouping step. For this purpose a support vector machine (SVM) or other supervised classifier can be used. Clustering labels may be used as initial training data. This process may be repeated, using the results from the most recent iteration of the classifier as the training for the next iteration, until it converges.

Although a clustering algorithm may be used to assign points to clusters, in some embodiments the points may be assigned to groups without using a clustering algorithm. In some embodiments, boundaries between groups of points may be determined without running a clustering algorithm.

In step S14, the clusters of points may be assigned to nucleotides. This assignment may be performed based on known characteristics of the labels. For example, in the plot of FIG. 4, it may be known that the label for a T has a high intensity and the lowest lifetime, the label for A has a low intensity and a moderate lifetime, the label for G has a high intensity and a moderate lifetime, and the label for C has the highest lifetime and a high intensity. The clusters of points may be assigned to bases using the position of the clusters relative to one another. For example, the cluster with the lowest lifetime may be assigned to T, the cluster with the highest lifetime may be assigned to C, the cluster with the lowest intensity may be assigned to A, and the remaining cluster may be assigned to G. The points in each cluster may be assigned the nucleotide of their cluster. By storing information about the time each measurement of intensity and temporal characteristic was performed, the nucleotide strand can be sequenced.

Figure 5:
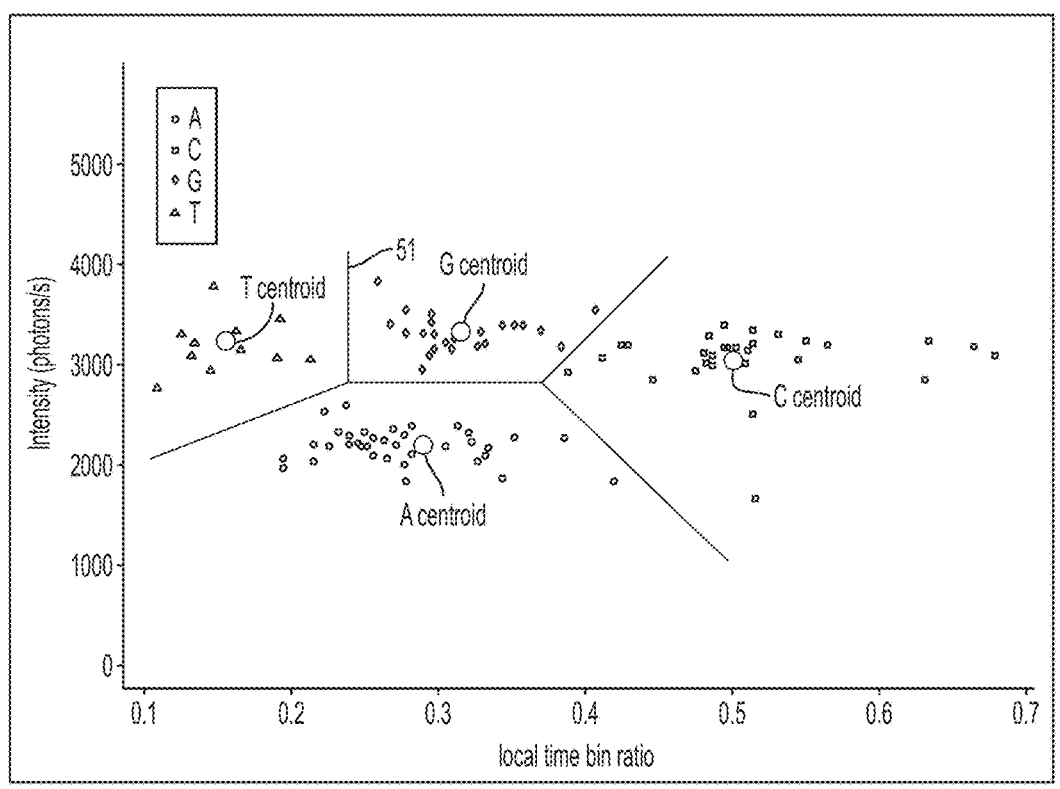
FIG. 5 is a plot showing boundaries and centroid positions for the clusters shown in FIG. 4, in accordance with some embodiments.

If the method is used to perform sequencing, the method may terminate at this point. If the method is used for calibration, the method may continue to step S15. The inventors have recognized and appreciated that if an initial calibration is performed, it is not necessary to run a clustering algorithm to assign all the points to nucleotides. In some embodiments, calibration criteria may be determined for assigning a point to a nucleotide type. As an example, following the clustering in step S13 or the assigning of the nucleotides in step S14, boundaries between the different types of nucleotides may be determined. The boundaries may be functions defining regions of a phase space as illustrated in FIG. 5. Axes of the phase space may include intensity, temporal parameter, emission wavelength, and/or excitation wavelength of the excitation laser pulses. As an example, line segments or curves in two-dimensional space may be selected that delineate the boundaries 51 between the different nucleotides, as shown in FIG. 5. In higher-dimensional space, the boundaries may be surfaces or higher-dimensional objects (termed "hyperplanes"). Once boundaries 51 are determined, the points can be assigned to nucleotides by evaluating their positions with respect to the boundaries, and clustering need not be performed. Accordingly, in some embodiments, a sequencing instrument may be calibrated to delineate the boundaries 51. The calibration process may be performed using the same set of labels as during sequencing of a nucleic acid. As another example of performing calibration in step S15, the centroids of the clusters may be determined, which can allow assigning the points to nucleotides based on which cluster has a centroid that is closest to an individual point. Regardless of the type of calibration criteria that are determined, the calibration criteria are then stored (e.g., in a memory of the instrument) for later use.

Calibration may be performed at any suitable time. In some embodiments, calibration may be desirable prior to first using the instrument, upon using a new set of labels, upon a change in environmental conditions in which the instrument is used, or after a period of use to account for aging of components of the instrument. The calibration may be performed in response to a request from a user, such as by pressing a button on the instrument or sending a calibration command to the instrument from another device, or automatically based on a schedule or on an as-needed basis in response to the instrument software determining the performance is sub-optimal. Once the calibration criteria are obtained, sequencing can be performed more quickly by evaluating the detected points with respect to the calibration criteria.

Figure 6:
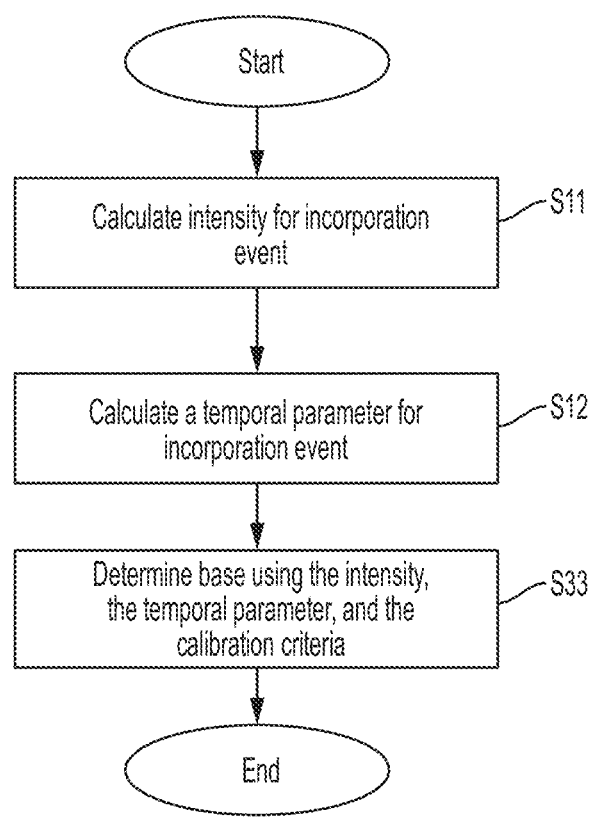
FIG. 6 is a flowchart of an algorithm implemented by a base caller to identify nucleotides based on one or more calibration criteria, in accordance with some embodiments.
Figure 7:
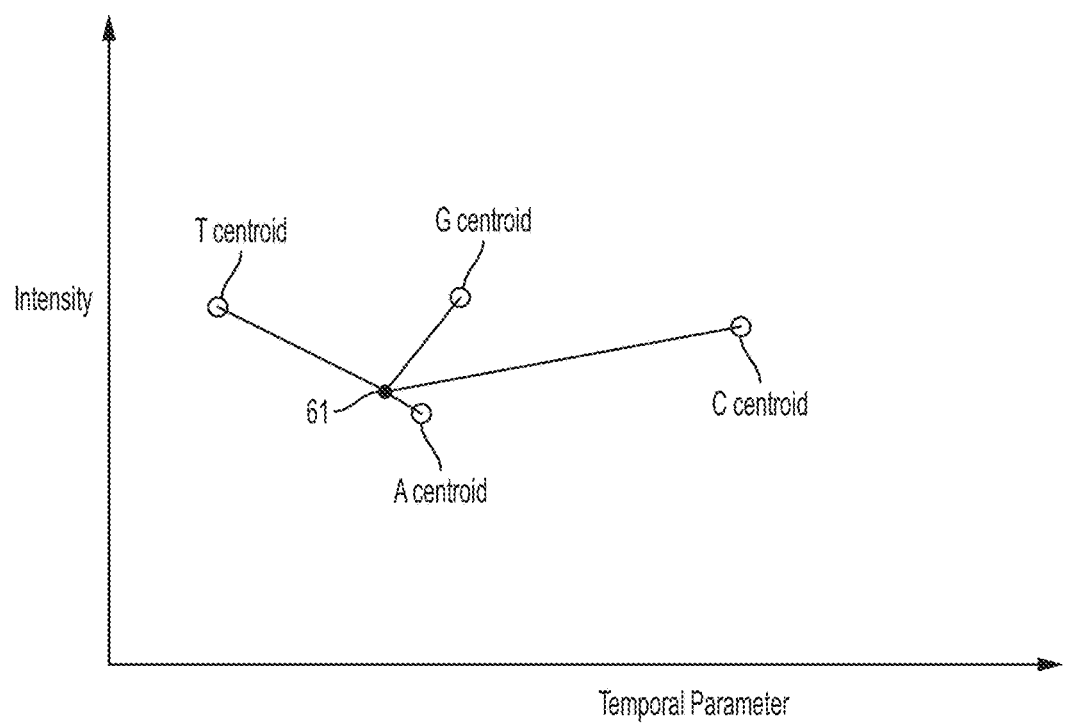
FIG. 7 is a plot of intensity versus temporal parameter illustrating relative distances of a point corresponding to a nucleotide incorporation event to centroid positions for different nucleotides, in accordance with some embodiments.

FIG. 6 shows a flowchart of an algorithm that may be used by the base caller to identify nucleotides based on one or more calibration criteria. The parameters of the light (e.g., intensity and a temporal parameter) may be determined in steps S11 and S12, which may be the same as those shown in FIG. 3, and steps S11 and S12 may be performed in any order, as discussed above. In step S33, nucleotides may be identified by evaluating the measured parameters of the light (e.g., intensity and temporal parameter) using the stored calibration information. For example, if the stored calibration information includes one or more boundaries between nucleotide clusters, the points can be assigned to nucleotides by comparing the points to the boundaries, which is more computationally efficient than performing clustering. As another example, the points can be assigned to nucleotides by calculating the distance of a point to each of the four centroids of the nucleotide clusters, then assigning the point to the nucleotide with the centroid that is the closest. This technique is illustrated in FIG. 7, which shows a point 61 representing a measured intensity and temporal parameter. Also shown in FIG. 6 are the centroids for the labels corresponding to the four nucleotides. To determine which centroid is closet, the distance from point 61 to each of the four centroids may be calculated, and the nucleotide is assigned to the point 61 which has its centroid the shortest distance from the point 61. As shown, point 61 is closest to the centroid for the label corresponding to the nucleotide "A." Accordingly, point 61 is determined to correspond to the nucleotide "A."

In some embodiments, identifying nucleotides includes performing clustering on a first portion of points associated with incorporation events and using calibration criteria to perform basecalls on a second portion of points. The first portion may include any suitable number of points to provide a desired level of accuracy in the calibration criteria.

In some embodiments a confidence level that a point corresponds to a particular type of nucleotide may be determined. As an example, the distance of a point from a centroid of a region, such as the centroids shown in FIG. 5, may be used to determine a confidence level for the point. Points having a small distance to the centroid may have a high confidence level indicating that the point is very likely correctly identified as corresponding to a nucleotide, while points having a larger distance from the centroid, or which are barely closer to one centroid than another are less likely to be correctly identified. In this example, the confidence level may be quantified based upon the distance between the point and the centroid, or based on comparing the distance between the point and the centroid with the distance between the point and one or more other centroids. As another example, if the calibration criteria includes one or more boundaries between clusters, the confidence level may be quantified by determining the distance between the point and one or more boundaries. Points that are closer to a boundary may be given a lower confidence level. In some embodiments, the confidence level for each nucleotide identification may be stored in addition to storing the nucleotide identification itself.

In some embodiments, the confidence level depends on the calibration criteria and how well the calibration criteria fit the calibration data. The more accurately the calibration criteria fit the calibration data, the higher the confidence levels may be for different points.

In some embodiments, the confidence level may depend on the time duration of the incorporation event associated with a point because the confidence level can depend on the signal-to-noise ratio of the pulse identified by the pulse caller. As an example, a long time duration may indicate that the pulse caller failed to identify two subsequent incorporation events, such as incorporation events of the same nucleotide type. In some embodiments, the base caller may communicate with the pulse caller to request that the pulse caller reevaluate the time duration of the incorporation event.

In some embodiments, previously-derived boundaries (e.g., an SVM model) may be applied to new pulse calls to determine the appropriate nucleotide incorporated at each pulse call event. Pulse call metrics are first scaled, then, the previously derived boundaries can be applied to classify that incorporation event.

In order to derive boundaries that generalize across the pulse call data from multiple pixels, it may be necessary to scale (or normalize) each set of pulse call data from each pixel in the array prior to including those data in the calibration dataset. By scaling the intensity metric, by clustering only on intensity, and using one or more of those clusters as the mean or median of intensity, one can normalize the intensity metric of all incoming pulse calls. This scaling, or normalization, is applied both during the calibration phase, as well as during the base calling phase using the stored calibration data. This has the benefit of not requiring boundaries be generated for each pixel in the array, which is a performance improvement, and enables scaling to very large arrays where all the data may not typically fit into RAM at once. A further benefit is a reduction in runtime, since a smaller number of pulses would need to be separated by intensity and scaled or normalized to the calibration data set. This approach also allows for fewer pulses to be stored and grouped, prior to establishing the scaling or normalization factors, thus allowing outputting base calls in near real time as the data is acquired from the pixel array.

Having described techniques that may be implemented by a pulse caller and a base caller to perform sequencing and/or calibration of a sequencing instrument, an example of a suitable sequencing instrument will now be described. In some embodiments, the instrument is configured to interface with an integrated device that includes an array of pixels. A surface of the integrated device has a plurality of sample wells, where a sample well is configured to receive a sample from a specimen placed on the surface of the integrated device. A specimen may contain multiple samples, and in some embodiments, different types of samples. The plurality of sample wells may have a suitable size and shape such that at least a portion of the sample wells receive one sample from a specimen. In some embodiments, the number of samples within a sample well may be distributed among the sample wells such that some sample wells contain one sample with others contain zero, two or more samples.

In some embodiments, a specimen may contain multiple single-stranded DNA templates, and individual sample wells on a surface of an integrated device may be sized and shaped to receive a single-stranded DNA template. Single-stranded DNA templates may be distributed among the sample wells of the integrated device such that at least a portion of the sample wells of the integrated device contain a single-stranded DNA template. The specimen may also contain tagged dNTPs which then enter in the sample well and may allow for identification of a nucleotide as it is incorporated into a strand of DNA complementary to the single-stranded DNA template in the sample well. In such an example, the "sample" may refer to both the single-stranded DNA and the tagged dNTP currently being incorporated by a polymerase. In some embodiments, the specimen may contain single-stranded DNA templates and tagged dNTPS may be subsequently introduced to a sample well as nucleotides are incorporated into a complementary strand of DNA within the sample well. In this manner, timing of incorporation of nucleotides may be controlled by when tagged dNTPs are introduced to the sample wells of an integrated device.

Excitation energy is provided from an excitation source located separate from the pixel array of the integrated device. The excitation energy is directed at least in part by elements of the integrated device towards one or more pixels to illuminate an illumination region within the sample well. A label may then emit emission energy when located within the illumination region and in response to being illuminated by excitation energy. In some embodiments, one or more excitation sources are part of the instrument of the system where components of the instrument and the integrated device are configured to direct the excitation energy towards one or more pixels.

Emission energy emitted by a sample may then be detected by one or more sensors within a pixel of the integrated device. Characteristics of the detected emission energy may provide an indication for identifying the marked associated with the emission energy. Such characteristics may include any suitable type of characteristic, including an arrival time of photons detected by a sensor, an amount of photons accumulated over time by a sensor, and/or a distribution of photons across two or more sensors. In some embodiments, a sensor may have a configuration that allows for the detection of one or more timing characteristics associated with a sample's emission energy (e.g., fluorescence lifetime). The sensor may detect a distribution of photon arrival times after a pulse of excitation energy propagates through the integrated device, and the distribution of arrival times may provide an indication of a timing characteristic of the sample's emission energy (e.g., a proxy for fluorescence lifetime). In some embodiments, the one or more sensors provide an indication of the probability of emission energy emitted by the label (e.g., fluorescence intensity). In some embodiments, a plurality of sensors may be sized and arranged to capture a spatial distribution of the emission energy. Output signals from the one or more sensors may then be used to distinguish a label from among a plurality of labels, where the plurality of labels may be used to identify a sample within the specimen.

A schematic overview of the system 2-100 is illustrated in FIGS. 2-1A and 2-1B. The system comprises an integrated device 2-102 that interfaces with an instrument 2-104. In some embodiments, instrument 2-104 may include one or more excitation sources 2-106 integrated as part of instrument 2-104. In some embodiments, an excitation source may be external to both instrument 2-104 and integrated device 2-102, and instrument 2-104 may be configured to receive excitation energy from the excitation source and direct it to the integrated device. The integrated device may interface with the instrument using any suitable socket for receiving the integrated device and holding it in precise optical alignment with the excitation source. The excitation source 2-106 may be configured to provide excitation energy to the integrated device 2-102. As illustrated schematically in FIG. 2-1B, the integrated device 2-102 has multiple pixels, where at least a portion of pixels 2-112 may perform independent analysis of a sample. Such pixels 2-112 may be referred to as "passive source pixels" since a pixel receives excitation energy from a source 2-106 separate from the pixel, where the source excites a plurality of pixels. A pixel 2-112 has a sample well 2-108 configured to receive a sample and a sensor 2-110 for detecting emission energy emitted by the sample in response to illuminating the sample with excitation energy provided by the excitation source 2-106. Sample well 2-108 may retain the sample in proximity to a surface of integrated device 2-102 to provide ease in delivery of excitation energy to the sample and detection of emission energy from the sample.

Optical elements for guiding and coupling excitation energy to the sample well 2-108 are located both on integrated device 2-102 and the instrument 2-104. Such source-to-well elements may comprise one or more grating couplers located on integrated device 2-102 to couple excitation energy to the integrated device and waveguides to deliver excitation energy from instrument 2-104 to sample wells in pixels 2-112. In some embodiments, elements located on the integrated device may act to direct emission energy from the sample well towards the sensor. Sample well 2-108, a portion of the excitation source-to-well optics, and the sample well-to-sensor optics are located on integrated device 2-102. Excitation source 2-106 and a portion of the source-to-well components are located in instrument 2-104. In some embodiments, a single component may play a role in both coupling excitation energy to sample well 2-108 and delivering emission energy from sample well 2-108 to sensor 2-110. Examples of suitable components, for coupling excitation energy to a sample well and/or directing emission energy to a sensor, to include in an integrated device are described in U.S. patent application Ser. No. 14/821,688 entitled "INTEGRATED DEVICE FOR PROBING, DETECTING AND ANALYZING MOLECULES," and U.S. patent application Ser. No. 14/543,865 entitled "INTEGRATED DEVICE WITH EXTERNAL LIGHT SOURCE FOR PROBING, DETECTING, AND ANALYZING MOLECULES," both of which are incorporated by reference in their entirety.

As illustrated in FIG. 2-1B, the integrated device comprises a plurality of pixels where a pixel 2-112 is associated with its own individual sample well 2-108 and at least one sensor 2-110. The plurality of pixels may be arranged in an array, and there may be any suitable number of pixels in the array. The number of pixels in integrated device 2-102 may be in the range of approximately 10,000 pixels to 1,000,000 pixels or any value or range of values within that range. In some embodiments, the pixels may be arranged in an array of 512 pixels by 512 pixels. Integrated device 2-102 and instrument 2-104 may include multi-channel, high-speed communication links for handling data associated with large pixel arrays (e.g., more than 10,000 pixels).

Instrument 2-104 interfaces with integrated device 2-102 through integrated device interface 2-114. Integrated device interface 2-114 may include components to position and/or align integrated device 2-102 to instrument 2-104 to improve coupling of excitation energy from excitation source 2-106 to integrated device 2-102. Excitation source 2-106 may be any suitable light source that is arranged to deliver excitation energy to at least one sample well. Examples of suitable excitation sources are described in U.S. patent application Ser. No. 14/821,688 entitled "INTEGRATED DEVICE FOR PROBING, DETECTING AND ANALYZING MOLECULES," which is incorporated by reference in its entirety. In some embodiments, excitation source 2-106 includes multiple excitation sources that are combined to deliver excitation energy to integrated device 2-102. The multiple excitation sources may be configured to produce multiple excitation energies or wavelengths. The integrated device interface 2-114 may receive readout signals from the sensors in the pixels located on the integrated device. The integrated device interface 2-114 may be designed such that the integrated device attaches to the instrument by securing the integrated device to the integrated device interface 2-114.

The instrument 2-104 includes a user interface 2-116 for controlling the operation of instrument 2-104. The user interface 2-116 is configured to allow a user to input information into the instrument, such as commands and/or settings used to control the functioning of the instrument. In some embodiments, the user interface 2-116 may include buttons, switches, dials, and a microphone for voice commands. Additionally, the user interface 2-116 may allow a user to receive feedback on the performance of the instrument and/or integrated device, such as proper alignment and/or information obtained by readout signals from the sensors on the integrated device. In some embodiments, the user interface 2-116 may provide feedback using a speaker to provide audible feedback, and indicator lights and/or display screen for providing visual feedback. In some embodiments, the instrument 2-104 includes a computer interface 2-118 used to connect with a computing device 2-120. Any suitable computer interface 2-118 and computing device 2-120 may be used. For example, the computer interface 2-118 may be a USB interface or a FireWire interface. The computing device 2-120 may be any general purpose computer, such as a laptop or desktop computer. The computer interface 2-118 facilitates communication of information between the instrument 2-104 and the computing device 2-120. Input information for controlling and/or configuring the instrument 2-104 may be provided through the computing device 2-120 connected to the computer interface 2-118 of the instrument. Output information may be received by the computing device 2-120 through the computer interface 2-118. Such output information may include feedback about performance of the instrument 2-104 and/or integrated device 2-112 and information from the readout signals of the sensor 2-110. The instrument 2-104 may also include a processing device 2-122 for analyzing data received from the sensor 2-110 and/or sending control signals to the excitation source 2-106. In some embodiments, the processing device 2-122 may comprise a general purpose processor, a specially-adapted processor (e.g., a central processing unit (CPU) such as one or more microprocessor or microcontroller cores, a field-programmable gate array (FPGA), an application-specific integrated circuit (ASIC), a custom integrated circuit, a digital signal processor (DSP), or a combination thereof.) In some embodiments, the processing of data from the sensor 2-110 may be performed by both the processing device 2-122 and the external computing device 2-120. In other embodiments, the computing device 2-120 may be omitted and processing of data from the sensor 2-110 may be performed solely by processing device 2-122.

A cross-sectional schematic of the integrated device 3-102 illustrating a row of pixels is shown in FIG. 3-1A. Each pixel 3-112 includes a sample well 3-108 and a sensor 3-110. The sensor 3-110 may be aligned and positioned to sample well 3-112 such that sensor 3-110 receives emission energy emitted by a sample within sample well 3-112. Examples of suitable sensors are described in U.S. patent application Ser. No. 14/821,656 entitled "INTEGRATED DEVICE FOR TEMPORAL BINNING OF RECEIVED PHOTONS," which is incorporated by reference in its entirety.

An excitation source coupled to the integrated device may provide excitation energy to one or more pixels of integrated device 3-102. FIG. 3-1B is a schematic illustrating coupling of excitation source 3-106 to integrated device 3-102 to provide excitation energy 3-130 (shown in dashed lines) to integrated device 3-102. FIG. 3-1B illustrates the path of excitation energy from excitation energy source 3-106 to a sample well 3-108 in pixel 3-112. Components located off of the integrated device may be used to position and align the excitation source 3-106 to the integrated device. Such components may include optical components including lenses, mirrors, prisms, apertures, attenuators, and/or optical fibers. Additional mechanical components may be included in the instrument to allow for control of one or more alignment components. Such mechanical components may include actuators, stepper motors, and/or knobs.

The integrated device includes components that direct the excitation energy 3-130 towards pixels in the integrated device. Within each pixel 3-112, excitation energy is coupled to the sample well 3-108 associated with the pixel. Although FIG. 3-1B illustrates excitation energy coupling to each sample well in a row of pixels, in some embodiments, excitation energy may not couple to all of the pixels in a row. In some embodiments, excitation energy may couple to a portion of pixels or sample wells in a row of pixels of the integrated device. Excitation energy may illuminate a sample located within a sample well. The sample may reach an excited state in response to being illuminated by the excitation energy. When a sample is in an excited state, the sample may emit emission energy and the emission energy may be detected by a sensor. FIG. 3-1B schematically illustrates the path of emission energy 3-140 (shown as solid lines) from sample well 3-108 to sensor 3-110 of pixel 3-112. Sensor 3-110 in pixel 3-112 may be configured and positioned to detect emission energy from sample well 3-108. In some embodiments, sensor 3-110 may include multiple sub-sensors.

A sample to be analyzed may be introduced into sample well 3-108 of pixel 3-112. The sample may be a biological sample or any other suitable sample, such as a chemical sample. The sample may include multiple molecules and the sample well may be configured to isolate a single molecule. In some instances, the dimensions of the sample well may act to confine a single molecule within the sample well, allowing measurements to be performed on the single molecule. An excitation source 3-106 may be configured to deliver excitation energy into the sample well 3-108, so as to excite the sample or at least one luminescent marker attached to the sample or otherwise associated with the sample while it is within an illumination area within the sample well 3-108.

When an excitation source delivers excitation energy to a sample well, at least one sample within the well may luminesce, and the resulting emission may be detected by a sensor. As used herein, the phrases "a sample may luminesce" or "a sample may emit radiation" or "emission from a sample" mean that a luminescent tag, marker, or reporter, the sample itself, or a reaction product associated with the sample may produce the emitted radiation.

One or more components of an integrated device may direct emission energy towards a sensor. The emission energy or energies may be detected by the sensor and converted to at least one electrical signal. The electrical signals may be transmitted along conducting lines in the circuitry of the integrated device connected to the instrument through the integrated device interface, such as integrated device interface 2-114 of instrument 2-104 shown in FIG. 2-1B. The electrical signals may be subsequently processed and/or analyzed. Processing or analyzing of electrical signals may occur on a suitable computing device either located on the instrument 2-104 or off instrument, such as computing device 2-120 shown in FIG. 2-1B.

In operation, parallel analyses of samples within the sample wells are carried out by exciting the samples within the wells using the excitation source and detecting signals from sample emission with the sensors. Emission energy from a sample may be detected by a corresponding sensor and converted to at least one electrical signal. The resulting signal, or signals, may be processed on the integrated device in some embodiments, or transmitted to the instrument for processing by the processing device and/or computing device. Signals from a sample well may be received and processed independently from signals associated with the other pixels.

In some embodiments, a sample may be labeled with one or more markers, and emission associated with the markers is discernable by the instrument. For example the sensor may be configured to convert photons from the emission energy into electrons to form an electrical signal that may be used to discern a lifetime that is dependent on the emission energy from a specific marker. By using markers with different lifetimes to label samples, specific samples may be identified based on the resulting electrical signal detected by the sensor.

A sample may contain multiple types of molecules and different luminescent markers may uniquely associate with a molecule type. During or after excitation, the luminescent marker may emit emission energy. One or more properties of the emission energy may be used to identify one or more types of molecules in the sample. Properties of the emission energy used to distinguish among types of molecules may include a fluorescence lifetime value, intensity, and/or emission wavelength. A sensor may detect photons, including photons of emission energy, and provide electrical signals indicative of one or more of these properties. In some embodiments, electrical signals from a sensor may provide information about a distribution of photon arrival times across one or more time intervals. The distribution of photon arrival times may correspond to when a photon is detected after a pulse of excitation energy is emitted by an excitation source. A value for a time interval may correspond to a number of photons detected during the time interval. Relative values across multiple time intervals may provide an indication of a temporal characteristic of the emission energy (e.g., lifetime). Analyzing a sample may include distinguishing among markers by comparing values for two or more different time intervals within a distribution. In some embodiments, an indication of the intensity may be provided by determining a number of photons across all time bins in a distribution.

The term "nucleic acid," as used herein, generally refers to a molecule comprising one or more nucleic acid subunits. A nucleic acid may include one or more subunits selected from adenosine (A), cytosine (C), guanine (G), thymine (T) and uracil (U), or variants thereof. In some examples, a nucleic acid is deoxyribonucleic acid (DNA) or ribonucleic acid (RNA), or derivatives thereof. A nucleic acid may be single-stranded or double stranded. A nucleic acid may be circular.

The term "nucleotide," as used herein, generally refers to a nucleic acid subunit, which can include A, C, G, T or U, or variants or analogs thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant or analogs thereof) or a pyrimidine (i.e., C, T or U, or variant or analogs thereof).

A nucleotide generally includes a nucleoside and at least 1, 2, 3, 4, 5, 6, 7, 8, 9, 10, or more phosphate ($PO_3$) groups. A nucleotide can include a nucleobase, a five-carbon sugar (either ribose or deoxyribose), and one or more phosphate groups. Ribonucleotides are nucleotides in which the sugar is ribose. Deoxyribonucleotides are nucleotides in which the sugar is deoxyribose. A nucleotide can be a nucleoside monophosphate or a nucleoside polyphosphate. A nucleotide can be a deoxyribonucleoside polyphosphate, such as, e.g., a deoxyribonucleoside triphosphate, which can be selected from deoxyadenosine triphosphate (dATP), deoxycytidine triphosphate (dCTP), deoxyguanosine triphosphate (dGTP), deoxyuridine triphosphate (dUTP) and deoxythymidine triphosphate (dTTP) dNTPs, that include detectable labels (e.g., fluorophores).

In some embodiments, techniques described herein may be carried out using one or more computing devices. Embodiments are not limited to operating with any particular type of computing device.

Figure 8:
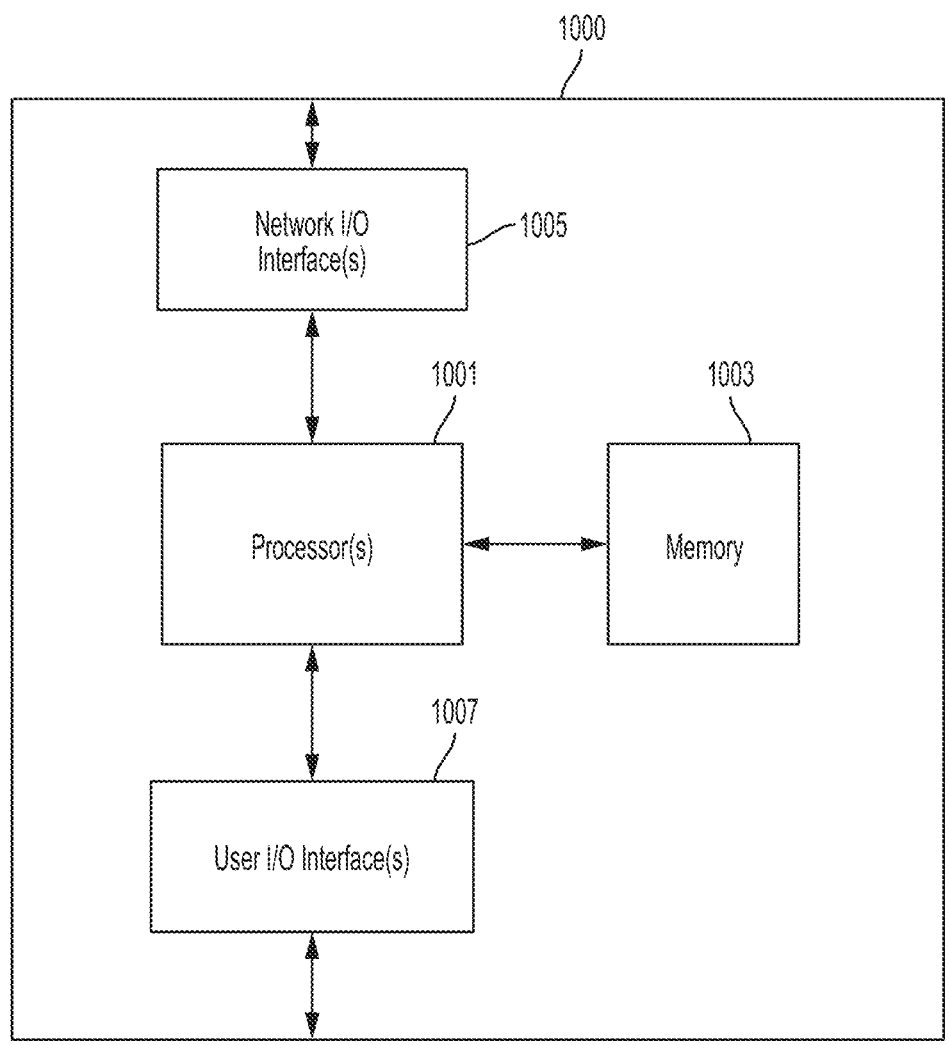
FIG. 8 is a block diagram of an illustrative computing device that may be used in implementing some embodiments of the technology described herein.

FIG. 8 is a block diagram of an illustrative computing device 1000. Computing device 1000 may include one or more processors 1001 and one or more tangible, non-transitory computer-readable storage media (e.g., memory 1003). Memory 1003 may store, in a tangible non-transitory computer-recordable medium, computer program instructions that, when executed, implement any of the above-described functionality. Processor(s) 1001 may be coupled to memory 1003 and may execute such computer program instructions to cause the functionality to be realized and performed.

Computing device 1000 may also include a network input/output (I/O) interface 1005 via which the computing device may communicate with other computing devices (e.g., over a network), and may also include one or more user I/O interfaces 1007, via which the computing device may provide output to and receive input from a user. The user I/O interfaces may include devices such as a keyboard, a mouse, a microphone, a display device (e.g., a monitor or touch screen), speakers, a camera, and/or various other types of I/O devices.

The above-described embodiments can be implemented in any of numerous ways. For example, the embodiments may be implemented using hardware, software or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein comprises at least one computer-readable storage medium (e.g., RAM, ROM, EEPROM, flash memory or other memory technology, CD-ROM, digital versatile disks (DVD) or other optical disk storage, magnetic cassettes, magnetic tape, magnetic disk storage or other magnetic storage devices, or other tangible, non-transitory computer-readable storage medium) encoded with a computer program (i.e., a plurality of executable instructions) that, when executed on one or more processors, performs the above-discussed functions of one or more embodiments. The computer-readable medium may be transportable such that the program stored thereon can be loaded onto any computing device to implement aspects of the techniques discussed herein. In addition, it should be appreciated that the reference to a computer program which, when executed, performs any of the above-discussed functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques discussed herein.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A sequencing instrument, comprising:
   a photodetector configured to receive light from luminescent labels during nucleotide incorporation events of a sequencing reaction, the luminescent labels being associated with nucleotides; and
   a processor configured to:
      obtain characteristics of the light, the characteristics including, for individual nucleotide incorporation events,
         a temporal characteristic of the light, the temporal characteristic representing a speed of decay of a probability of photon emission by a luminescent label after excitation; and
         an intensity characteristic of the light, wherein the temporal characteristic and the intensity characteristic are characteristics of light received from a luminescent label during a nucleotide incorporation event; and
   wherein the temporal characteristic and the intensity characteristic are used to perform one or more of: identifying individual nucleotides, and calibrating the sequencing instrument, and
   wherein the intensity characteristic represents a quantity of photogenerated charge carriers produced over time by the photodetector from the light received from the luminescent label during the nucleotide incorporation event.

2. The sequencing instrument of claim 1, wherein the temporal characteristic and the intensity characteristic are used to perform identifying individual nucleotides, and wherein the identifying of the individual nucleotides comprises:
   grouping points representing the characteristics into groups of points, individual points representing at least the temporal characteristic and the intensity characteristic for a corresponding nucleotide incorporation event; and
   assigning the groups of points to individual nucleotides.

3. The sequencing instrument of claim 2, wherein the points are grouped using a clustering algorithm.

4. The sequencing instrument of claim 3, wherein the clustering algorithm performs k-means clustering in which k is greater than or equal to four.

5. The sequencing instrument of claim 3, wherein the groups of points are assigned to the individual nucleotides based on predetermined light-emitting characteristics of the luminescent labels.

6. The sequencing instrument of claim 1, wherein the temporal characteristic and the intensity characteristic are used to perform identifying individual nucleotides, and wherein the identifying of the individual nucleotides comprises:
   determining one or more criteria distinguishing groups of points representing the characteristics, individual points representing the temporal characteristic and the intensity characteristic for a corresponding nucleotide incorporation event;
   assigning the groups to respective nucleotides to produce nucleotide assignments for the groups; and
   assigning the points to nucleotides based on the one or more criteria and the nucleotide assignments for the groups.

7. The sequencing instrument of claim 1, wherein the temporal characteristic and the intensity characteristic are used to perform identifying individual nucleotides, wherein the identifying of the individual nucleotides comprises assigning the nucleotide incorporation events to nucleotides by evaluating the temporal characteristic and the intensity characteristic in view of stored criteria for a sequencing instrument, and distinguishing between the characteristics of the light for the luminescent labels.

8. The sequencing instrument of claim 7, wherein the stored criteria comprises one or more boundaries between characteristics of the luminescent labels for different nucleotides, and the assigning of the nucleotide incorporation events comprises comparing a point representing the temporal characteristic and the intensity characteristic with the one or more boundaries.

9. The sequencing instrument of claim 7, wherein the stored criteria comprises centroids of groups of points, each group corresponding to a respective nucleotide, and the assigning of the nucleotide incorporation events comprises:
   determining distances between a point representing the temporal characteristic and the intensity characteristic for an incorporation event to the centroids; and
   assigning the nucleotide incorporation event to a nucleotide with a centroid closest to the point.

10. The sequencing instrument of claim 7, wherein the stored criteria are calibration criteria stored in non-volatile memory.

11. The sequencing instrument of claim 1, wherein the temporal characteristic and the intensity characteristic are used to perform identifying of individual nucleotides, wherein the identifying the individual nucleotides comprises:
   determining one or more criteria distinguishing groups of points representing the characteristics of the nucleotide incorporation events, individual points representing the temporal characteristic and the intensity characteristic for a corresponding nucleotide incorporation event;
   assigning the groups to respective nucleotides to produce nucleotide assignments for the groups; and
   assigning the points to nucleotides based on the one or more criteria and the nucleotide assignments for the groups.

12. The sequencing instrument of claim 1, further comprising an excitation source to excite the luminescent labels.

13. The sequencing instrument of claim 12, wherein the excitation source comprises a laser.

14. The sequencing instrument of claim 12, further comprising a plurality of sample wells configured to receive excitation energy from the excitation source.

* * * * *